US00PP28394P3

(12) United States Plant Patent
Warner

(10) Patent No.: US PP28,394 P3
(45) Date of Patent: Sep. 19, 2017

(54) SHRUB ROSE PLANT NAMED 'CHEWBULLSEYE'

(50) Latin Name: ***Rosa* hybrid**
Varietal Denomination: ChewBullseye

(71) Applicant: Christopher Hugh Warner, Brockton (GB)

(72) Inventor: Christopher Hugh Warner, Brockton (GB)

(73) Assignee: Spring Meadow Nursery Inc., Grand Haven, MI (US)

( * ) Notice: Subject to any disclaimer, the term of this patent is extended or adjusted under 35 U.S.C. 154(b) by 11 days.

(21) Appl. No.: 14/757,058

(22) Filed: Nov. 12, 2015

(65) Prior Publication Data

US 2017/0142877 P1 May 18, 2017

(51) Int. Cl.
*A01H 5/02* (2006.01)

(52) U.S. Cl.
USPC ..... Plt./102

(58) Field of Classification Search
USPC ..... Plt./101, 102
See application file for complete search history.

*Primary Examiner* — Susan McCormick Ewoldt
(74) *Attorney, Agent, or Firm* — Cassandra Bright

(57) ABSTRACT

A new and distinct *Rosa* cultivar, for garden use named 'ChewBullseye' is disclosed, characterized by a compact bushy plant, producing unique yellow-orange flowers with a distinctive red eye. Plants have an above average resistance to diseases and repeat bloom rapidly. Flowers are typically 6 to 7.5 cm in diameter. The new variety is a *Rosa*, normally produced as an outdoor garden or container plant.

3 Drawing Sheets

Latin name of the genus and species: *Rosa* hybrid.
Variety denomination: 'ChewBullseye'.

BACKGROUND OF THE INVENTION

The new *Rosa* cultivar is a product of a cross-breeding program conducted by the inventor, Christopher Hugh Warner in Brockton, Newport Shromshire, United Kingdom. The objective of the breeding program was to produce new *Rosa* varieties for ornamental commercial applications. The cross resulting in this new variety was made during June of 2006.

The seed parent is the unpatented variety referred to as *Rosa* hybrid 'Belting Pink'. The pollen parent is the unpatented variety referred to as *Rosa* hybrid 'Golden Age'. The new variety was discovered in June of 2007 by the inventor in a group of seedlings resulting from the 2006 crossing, in a research greenhouse in Brockton, Newport Shromshire, United Kingdom.

Asexual reproduction of the new cultivar was performed by vegetative cuttings. This was first performed at a research greenhouse in Brockton, Newport Shromshire in Summer of 2008 and has shown that the unique features of this cultivar are stable and reproduced true to type in successive generations.

SUMMARY OF THE INVENTION

The cultivar 'ChewBullseye' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ChewBullseye' These characteristics in combination distinguish 'ChewBullseye' as a new and distinct *Rosa* cultivar:

1. Unique creamy yellow-orange flowers with a red spot in center of flower.
2. Compact, bushy plant.
3. Rapid repeat flowering.
4. Abundant shiny foliage
5. Strong disease resistance.
6. Flower size near 6 to 7.5 cm in diameter Plants of the new cultivar 'ChewBullseye' are similar to plants of the seed parent in most horticultural characteristics, however, plants of the new cultivar 'ChewBullseye' differ in the following:

1. Flower color is yellow-orange with a distinctive red eye. The seed parent has a pink colored flower, with a dark pink eye.

Plants of the new cultivar 'ChewBullseye' are similar to plants of the pollen parent in most horticultural characteristics, however, plants of the new cultivar 'ChewBullseye' differ in the following;

1. Flower color is yellow-orange with a red eye. The pollen parent has a bright yellow colored flower, with a dark red eye.
2. The dark red eye of the parent variety is larger than the red eye of the new variety.

COMMERCIAL COMPARISON

Plants of the new cultivar 'ChewBullseye' can also be compared to the commercial variety *Rosa* 'ChewHocan', U.S. Plant Pat. No. 26,194. These varieties are similar in most horticultural characteristics; however 'ChewBullseye' differs in the following:

1. Flower color is yellow-orange with red center. Comparator flower is soft yellow.

2. The new variety has a larger flower than this comparator.
3. Flower color of the new variety fades as it ages. Comparator has strong color retention as it ages.

BRIEF DESCRIPTION OF THE PHOTOGRAPHS

The accompanying photograph in FIG. 1 illustrates in full color typical flowers of 'ChewBullseye', including the range of colors aging flowers exhibit.

Figure 1:
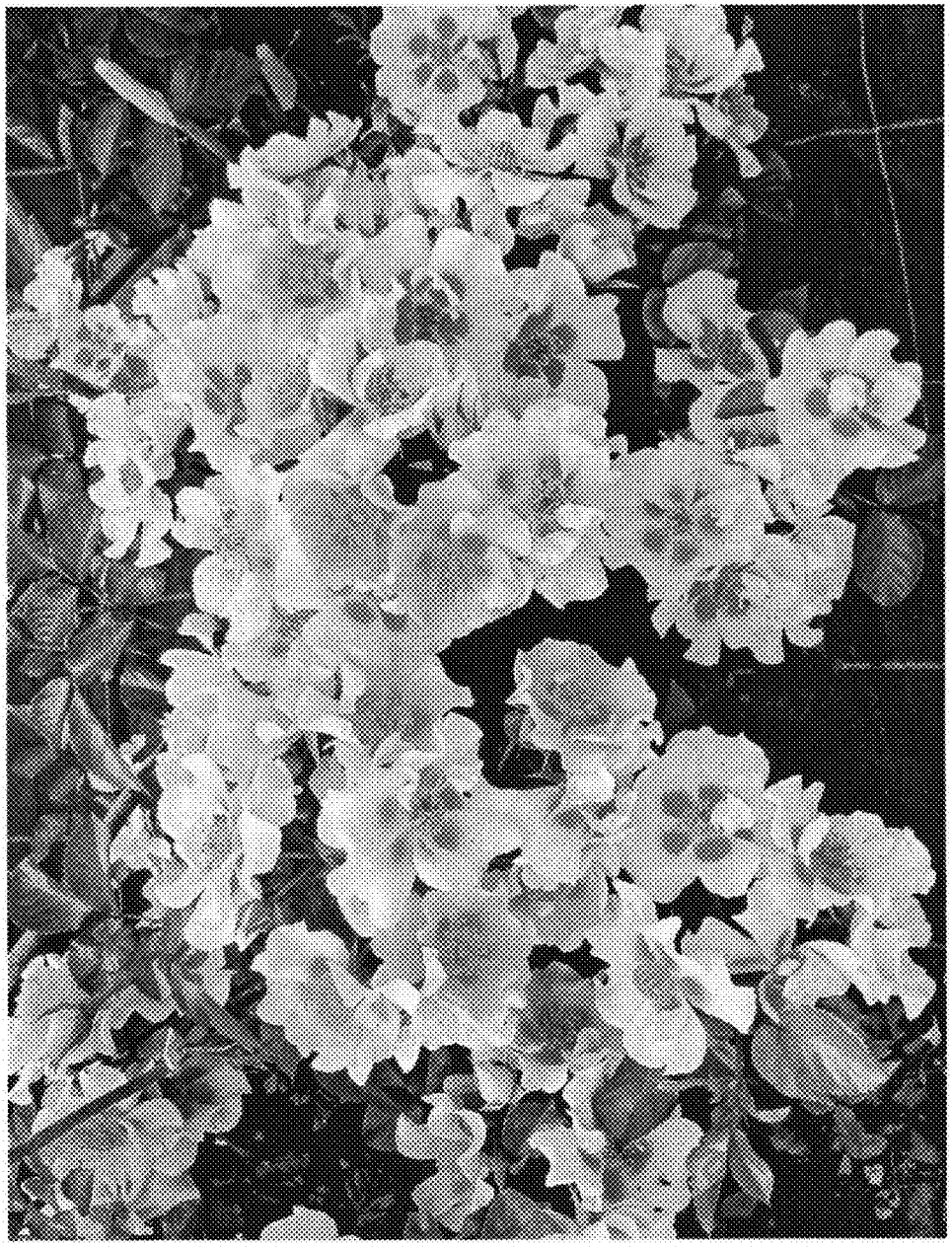
Figure 2:
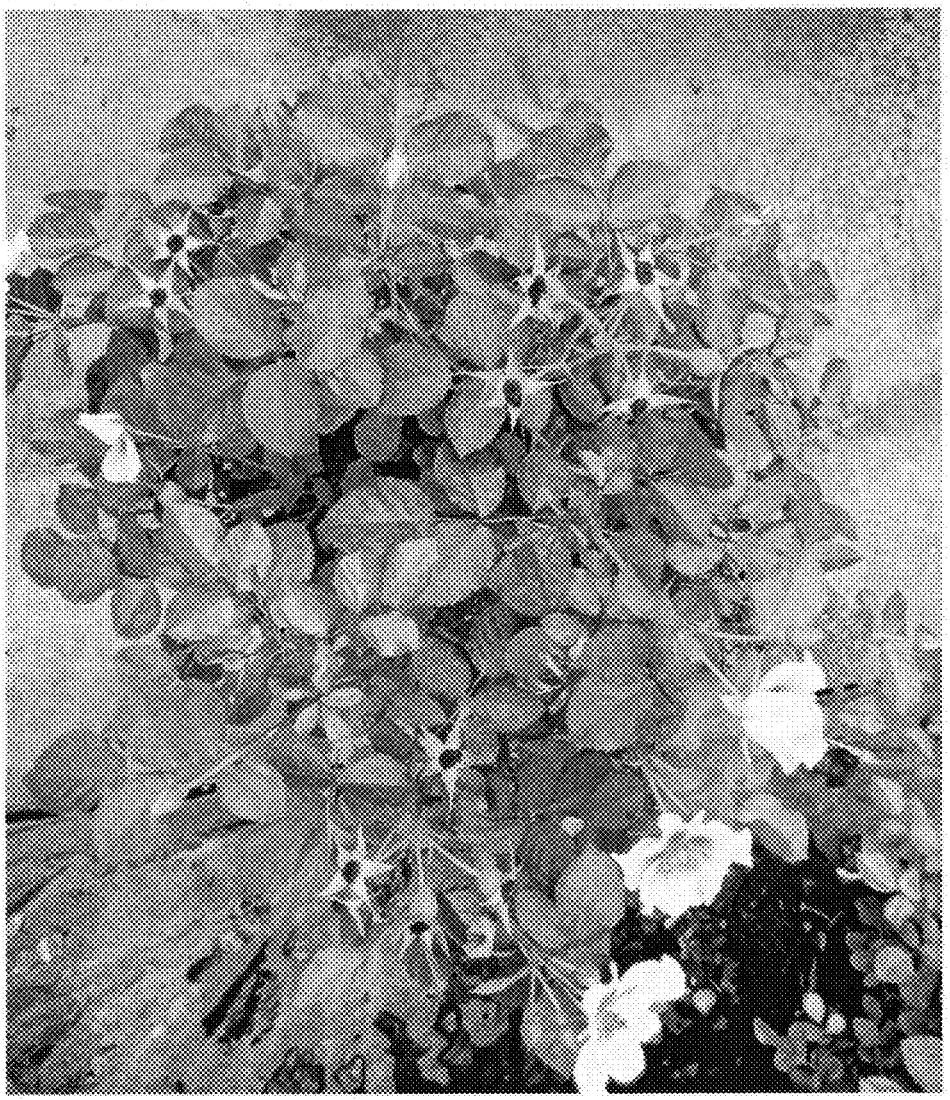
FIG. 2 illustrates a typical 1 year old plant of the new variety, in a 2 gallon pot.
Figure 3:
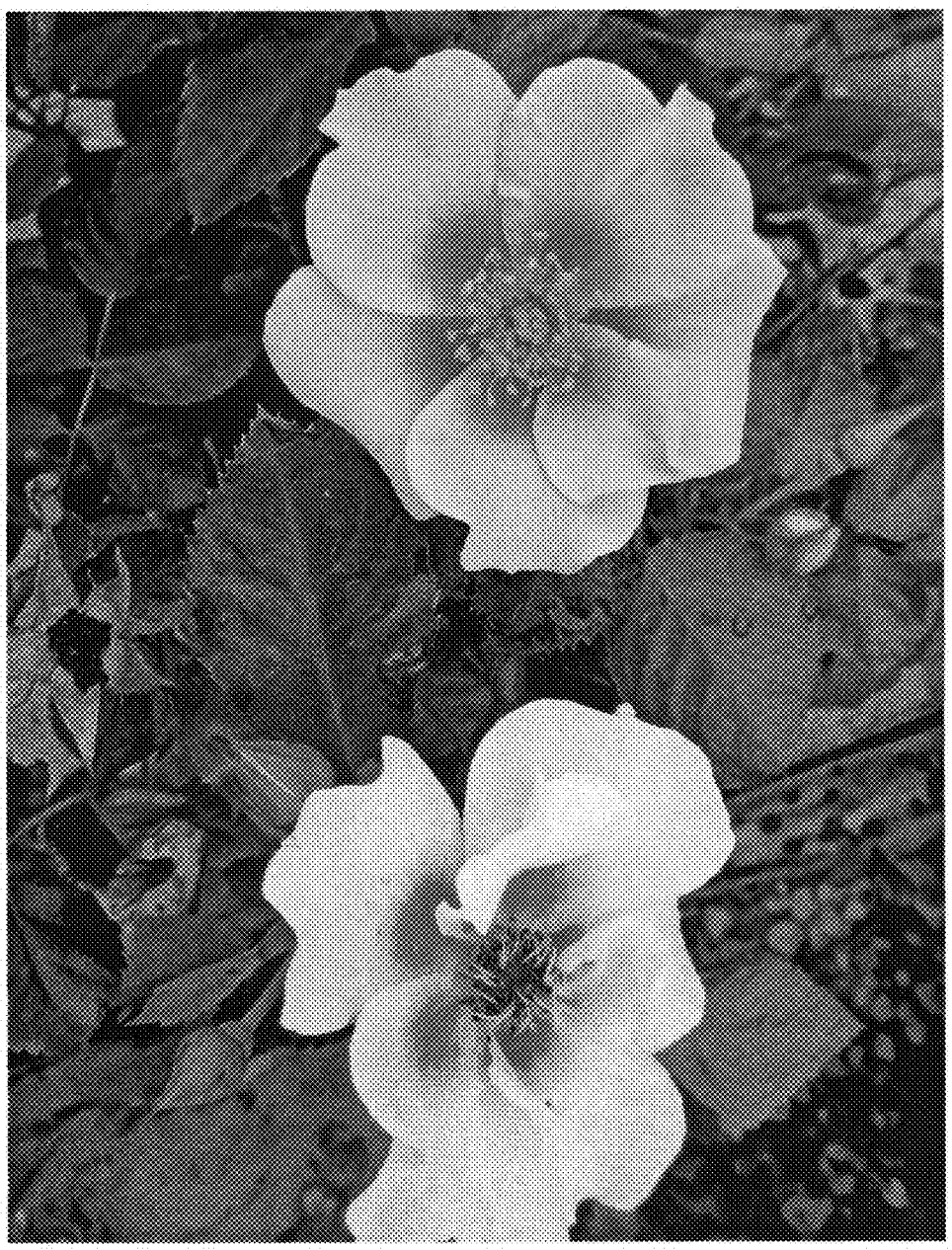
FIG. 3 illustrates a close up of a single mature flower and a single fading flower. The uppermost flower is the mature flower, the lower flower is the fading flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'ChewBullseye' plants grown in a poly house greenhouse, in Grand Haven, Mich. The growing temperature ranged from approximately 18° C. to 27° C. during the day and from approximately 5° C. to 10° C. during the night. General light conditions are bright, normal sunlight. Measurements and numerical values represent averages of typical plant types.

Botanical classification: *Rosa* 'ChewBullseye'.

Commercial classification: Shrub.

PROPAGATION:

Time to initiate roots: About 30 days at approximately 20° C.

Time to produce a rooted young plant: About 120 days at approximately 20° C.

PLANT

Age of plant described: Approximately 2 years.

Plant habit: Compact, mounding garden rose.

Container size of plant described: 3 gallon.

Height: 45 cm.

Plant spread: 47 cm.

Rootstock: Un-grafted, plants grown on own roots.

Growth rate: Moderate.

Branching arrangement: Abundant basal branching. Approximately 10 to 12 basal stems. Dense lateral branching.

Main basal stems:

- *Diameter*.—Approximately 1 cm, after 2 years.
- *Length*.—Approximately 40-47 cm.
- *Color*.—Near Yellow-Green RHS 144A.
- *Texture*.—Glabrous, thorny.
- *Thorns*.—Approximately density/quantity of thorns: 2 to 5 per linear cm. Shape: Very narrow, acicular at middle and apex. Oblanceolate base. Color of thorns: Apex near RHS Red 46A, mid section Red 48A, base Green-Yellow 1B. Diameter: Average 6 mm Height: Average 10 mm.

FOLIAGE

Leaf:

- *Arrangement*.—Alternate.
- *Quantity*.—Approximately 9-10 per main branch.
- *Average length*.—Approximately 9.0 cm.
- *Average width*.—Approximately 6.0 cm.

Leaflet:

- *Quantity*.—Approximately 7 per leaf.
- *Average length*.—Terminal Length: Approximately 3.5 cm. Lateral Length: Approximately 3.0 cm.
- *Average width*.—Terminal Width: Approximately 2.5 cm. Lateral Width: Approximately 2.0 cm.
- *Shape of blade*.—Elliptic.
- *Apex*.—Mucronate.
- *Base*.—Obtuse.
- *Margin*.—Serrulate.
- *Appearance of top surface*.—Glossy.
- *Appearance of bottom surface*.—Matte.
- *Texture of top surface*.—Glabrous.
- *Texture of bottom surface*.—Glabrous, small thorns on midrib.
- *Leaf internode length*.—Average 5 cm.
- *Color*.—Young foliage upper side: Near Green RHS 139A. Young foliage under side: Near Green RHS 138B. Mature foliage upper side: Near Green RHS 139A. Mature foliage under side: Near Green RHS 138B.

Venation:

- *Type*.—Pinnate.
- *Venation color upper side*.—Midrib near RHS Yellow-Green 145A; blends to RHS Green 139A towards margin.
- *Venation color under side*.—Near RHS Yellow-Green 145C.

Petiole:

- *Length*.—2.5 cm.
- *Width*.—0.35 cm.
- *Color*.—Near RHS Yellow-Green 145, upper and lower surfaces.
- *Texture*.—Slight waxy with minute thorns, upper and lower surfaces.
- *Other characteristics*.—Stipulate with adnate stipule 1 cm diameter.

Leaflet petiole:

- *Length*.—1 mm.
- *Width*.—0.5 mm.
- *Color*.—Near RHS Yellow-Green 145A, upper and lower surfaces.
- *Texture*.—Glabrous.

Stipule:

- *Quantity*.—2.
- *Shape*.—Winglike off of petiole; deltoid.
- *Apex*.—Subulate.
- *Base*.—Attenuate.
- *Margin*.—Serrulate.
- *Length*.—1 to 1.5 cm.
- *Width*.—4 mm.
- *Texture*.—Glabrous, upper and lower surfaces.

*Color*.—Upper surface near RHS Green 139A, lower surfaces near Green 138A.

FLOWER

Natural flowering season: Spring through summer.

Arrangement: Single blooms occur at terminal branch ends. 1 to 3 flowers occur at terminus. Flower shape irregularly rounded.

Flower size:

*Diameter*.—Approximately 6 to 7.5 cm.

*Depth*.—Approximately 3 cm.

Peduncle:

*Length*.—3 cm.

*Diameter*.—2.5 cm.

*Strength*.—Strong.

*Angle*.—Upright, approximately 90°.

*Texture*.—Glabrous.

*Color*.—Yellow-Green 145A.

Petals:

*Petal arrangement*.—Rotate, overlapping, whorled.

*Length*.—3.0-3.5 cm.

*Width*.—3.0-3.5 cm.

*Shape*.—Widely ovate.

*Margin*.—Entire.

*Apex*.—Mucronate.

*Base*.—Obtuse.

*Petal quantity*.—Average 5-7.

*Texture*.—Glabrous, silky, upper and lower surfaces.

*Aspect*.—Moderate undulation.

Color:

*Petals*.—When opening: Upper surface: Near RHS Yellow-Orange 14A; Center (of about 0.12 cm diameter) near RHS Red 44A. Lower surface: Near RHS Yellow-Orange 14C. Fully opened: Upper surface: Near RHS Yellow-Orange 14D; Center (of about 0.12 cm diameter) near RHS Red 39A. Lower surface: Near RHS Yellow 11C. Color Changes when aging: Upper surface: Fades to near RHS Yellow 11D. Center near Red 55C and 55D. Lower Surfaces: Fades to near RHS Yellow 11D.

Bud:

*Shape*.—Ovate.

*Length*.—Approximately 2.0 cm.

*Diameter*.—Approximately 0.11 cm.

*Color*.—Near RHS Yellow-Green 144A.

Sepals:

*Length*.—2.0 cm.

*Width*.—0.7 cm.

*Shape*.—Lanceolate.

*Color*.—Immature: Interior Surface: Near RHS Yellow-Green 144A. Exterior Surface: Near RHS Yellow-Green 145A. Mature: Interior Surface: Near RHS Yellow-Green 144A. Exterior Surface: Near RHS Yellow-Green 145A.

*Texture*.—Smooth, waxy.

*Fragrance*.—Light fresh scent.

REPRODUCTIVE ORGANS

Stamens:

*Number*.—110.

*Filament length*.—Approximately 0.9 cm.

*Filament color*.—Near RHS Yellow-Orange 15B.

Anthers:

*Length*.—0.2 cm.

*Shape*.—Club-like.

*Color*.—Near RHS Yellow-Orange 22A.

*Pollen*.—Color: Near RHS Yellow-Orange 22A. Quantity: 42 fused in the center.

Pistil:

*Quantity*.—42, fused in the center. Style: Length: Approximately 4 mm. Color: Near RHS Red 50A, base near Green-Yellow 1D. Stigma: Shape: Globular cluster. Color: Near RHS Yellow 7A.

Receptacle:

*Height*.—11 mm.

*Diameter*.—6.5 mm.

*Shape*.—Obovate.

*Color*.—Near RHS Green 144A.

OTHER CHARACTERISTICS

Seeds and fruits: Not observed to date.

Temperature tolerance: Tolerant of low temperatures to −31° C., tolerant of high temperatures to at least 38° C.

Drought tolerance: No tolerance for drought observed to date.

Disease/pest resistance: Above average disease resistance to normal diseases typical of garden roses. Average tolerance for typical garden pests.

What is claimed is:

1. A new and distinct cultivar of *Rosa* plant named 'ChewBullseye' as herein illustrated and described.

* * * * *